United States Patent
Brook et al.

(10) Patent No.: US 8,648,211 B2
(45) Date of Patent: Feb. 11, 2014

(54) SURFACE-MODIFYING SILICONE ELASTOMERS

(76) Inventors: Michael A. Brook, Ancaster (CA); Yongxin Wang, Hamilton (CA); Yang Chen, Ancaster (CA)

( * ) Notice: Subject to any disclaimer, the term of this patent is extended or adjusted under 35 U.S.C. 154(b) by 0 days.

(21) Appl. No.: 13/392,568

(22) PCT Filed: Aug. 27, 2010

(86) PCT No.: PCT/CA2010/001319
§ 371 (c)(1),
(2), (4) Date: May 14, 2012

(87) PCT Pub. No.: WO2011/022827
PCT Pub. Date: Mar. 3, 2011

(65) Prior Publication Data
US 2012/0226001 A1    Sep. 6, 2012

Related U.S. Application Data

(60) Provisional application No. 61/237,410, filed on Aug. 27, 2009.

(51) Int. Cl.
C08G 77/38    (2006.01)
C07F 7/00    (2006.01)

(52) U.S. Cl.
USPC ............ 556/445; 556/450; 556/453; 525/477

(58) Field of Classification Search
None
See application file for complete search history.

(56) References Cited

U.S. PATENT DOCUMENTS

| 6,221,922 B1 | 4/2001 | Policello et al. |
| 6,300,452 B1 | 10/2001 | Jukarainen et al. |
| 2006/0263612 A1 | 11/2006 | Chen et al. |
| 2007/0148244 A1* | 6/2007 | Kunzler et al. ............... 424/486 |

FOREIGN PATENT DOCUMENTS

| JP | 11049960 A * | 2/1999 | ............ C08L 83/07 |
| WO | 03002809 A1 | 1/2003 | |
| WO | 2007056427 A3 | 5/2007 | |

OTHER PUBLICATIONS

Guo et al. "Surface-hydrophilic and protein-resistant silicone elastomers prepared by hydrosilylation of vinyl poly(ethylene glycol) on hydrosilanes-poly(dimethylsiloxane) surfaces" Colloids and Surfaces A: Physicochem. Eng. Aspects 308, 2007, 129-135.*
International Preliminary Report on Patentability dated Mar. 8, 2012 for PCT/CA2010/001319.
Fujita, Makoto et al., "An approach to a solid polymer electrolyte by sol-gel condensation: preparation of a new class of poly(ethylene oxide)-polysiloxane hybrid", Polymer Communications, 1989, 30(7), 200-201.

(Continued)

*Primary Examiner* — Robert S Loewe
(74) *Attorney, Agent, or Firm* — Bereskin & Parr LLP/S.E.N.C.R.L., s.r.l.; Palricia Folkins

(57) ABSTRACT

The present disclosure describes compounds of Formula (I) wherein m is 1 to 6, n is 6 to 10 and $R^1$ is a straight or branch chain siloxane, their use in methods to modify the surface of hydrophobic substrates to render the substrates superhydrophilic and surface-modified substrates.

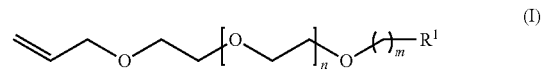

19 Claims, 8 Drawing Sheets

(56) References Cited

OTHER PUBLICATIONS

Dong A., Mao, G., "Nanoscale aggregate structures of trisiloxane surfactants at the solid-liquid interface", Langmuir 20 (7), 2004, pp. 2695-2700.

Chung D., Lim, J.C., "Study on the effect of structure of polydimethylsiloxane grafted with polyethyleneoxide on surface activities", Colloids and Surfaces: A Physicochemical and Engineering Aspects, 336 (1-3), 2008, pp. 35-40.

Nikolov A.D., et al., "Superspreading driven by Marangoni flow", Adv. Colloid Interface Sci., 96 (103), 2002, pp. 325-338.

Hou W., Wang, Q., "Wetting behaviour of a SiO(2)-polystyrene nanocomposite surface" J. Colloid Interface Sci., 316 (1), 2007, pp. 206-209.

Hou W., Wang, Q., "From superhydrophilicity to superhydrophbicity: the wetting behaviour of a methylsilicone/ phenolic resin/silica composite surface", Langmuir 23 (19), 2007, pp. 9695-9698.

* cited by examiner

SURFACE-MODIFYING SILICONE ELASTOMERS

CROSS-REFERENCE TO RELATED APPLICATIONS

This application is a national phase entry of PCT/CA2010/001319, filed Aug. 27, 2010, which claims priority from U.S. Provisional patent application Ser. No. 61/237,410, filed on Aug. 27, 2009 the contents of each of these applications being incorporated herein by reference in their entirety.

FIELD

The present disclosure relates to compounds that, when grafted onto a polymer surface, renders that surface superhydrophilic. More particularly, the present disclosure relates to compounds for rendering the surface of silicone elastomers superhydrophilic.

INTRODUCTION

Polydimethylsiloxane (PDMS) elastomers are soft, flexible materials possessing a variety of advantageous properties that include synthetic flexibility, optical transparency, biocompatibility, and high oxygen permeability. However, the low surface energy exhibited by silicones can be challenging for use in certain applications such as soft lithography and biomaterials. For example, the intrinsic hydrophobicity of PDMS stamps prevents polar "inks" from wetting out their surface, resulting in defective patterns generated from the stamps.[1] As for contact lenses, poor surface wettability make them susceptible to fouling by proteins or lipids, which can be detrimental to nutrient permeability and patient comfort.[2,3]

Two main strategies have been used to increase silicone surface hydrophilicity. The first of these include oxygen plasma treatment,[4-7] UV irradiation,[8-10] and corona discharge,[11,12] all of which induce surface hydroxylation of PDMS via high energy irradiation. One drawback of these methodologies is that physical damage to the surface may occur.[13] In an alternative second strategy, hydrophilic materials may be absorbed,[14,15] grafted (e.g., poly(ethylene glycol)[16]) or copolymerized (e.g., plasma polymerization[17]),[18] onto the silicone surface. Both strategies have drawbacks. Silicone polymers, with their high mobility[19,20] and stability at air interfaces, generally undergo surface 'reversion,' such that hydrophilic materials become buried under a mobile silicone layer that migrates to the air interface.[21,22] Although silicone elastomers can be temporarily made hydrophilic, with water contact angles of 0°, the surfaces revert to their hydrophobic nature with much higher contact angles over short periods of time.[18,22-24]

Superwetters are a class of silicone surfactants that have a remarkable ability to facilitate dispersion of water across hydrophobic surfaces, for example, to disperse pesticides across the surfaces of hydrophobic leaf surfaces.[25,26] The compounds typically have an oligo(ethylene oxide) terminated at one end with a hydrophobic trisiloxane siloxane head group, and various organic groups at the other (FIG. 1A).[27]

The preparation of superhydrophilic surfaces (water contact angle <10°) has attracted much attention in the past years.[28-30] Such surfaces can be achieved by use of a responsive/dynamic hydrophilic layer; static hydrophilic layers are not typically effective. A dynamic layer is one that can develop a driving force to facilitate water spreading over the material's surface. For instance, capillary forces between surface-bound nanoparticles of a bimodal distribution led to efficient water wetting yielding a 'superhydrophilic' surface.[29]

SUMMARY

In the present work, a surface modifying compound was prepared in which an allyl group was placed at one end of an oligo(ethylene glycol) chain and a siloxane was placed on the other end. The allyl group permits grafting of the compound to surfaces that can be made to react with the allyl functional group. Examples of such surfaces include silicone elastomers comprising Si—H groups which can react with the allyl group under hydrosilylation reaction conditions.

Accordingly, the present disclosure includes a compound of the formula (I):

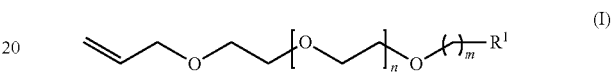

wherein
n is 6, 7, 8, 9 or 10;
m is 1, 2, 3, 4, 5 or 6; and
$R^1$ is a straight or branched chain siloxane.

The present disclosure also includes a method of modifying a surface of a substrate comprising grafting one or more compounds of Formula (I) to the substrate. In an embodiment, the grafting is done by reacting the substrate and the one or more compounds of Formula (I) under conditions to form a covalent attachment therebetween. In an embodiment, the covalent attachment is formed by a reaction between the allyl group on the one or more compounds of Formula (I) and one or more functional groups on the substrate. In an embodiment, the substrate is one that can be made to react with one or more compounds of Formula (I). For example, the substrate is a silicone polymer comprising Si—H functional groups that react with the allyl group on the one or more compounds of Formula (I) under hydrosilylation reaction conditions.

The present disclosure also includes a use of one or more compounds of Formula (I) to modify a surface of a substrate.

The present disclosure also includes a substrate that has been surface modified by grafting of one or more compounds of Formula (I) as defined above onto its surface. In an embodiment, the substrate is PDMS. In an embodiment, the substrate has been surface modified to have a water contact angle of 10° or less.

Other features and advantages of the present application will become apparent from the following detailed description. It should be understood, however, that the detailed description and the specific examples, while indicating embodiments of the application, are given by way of illustration only, since various changes and modifications within the spirit and scope of the application will become apparent to those skilled in the art from this detailed description.

DRAWINGS

The application will now be described in greater detail with reference to the drawings in which.

Figure 6:
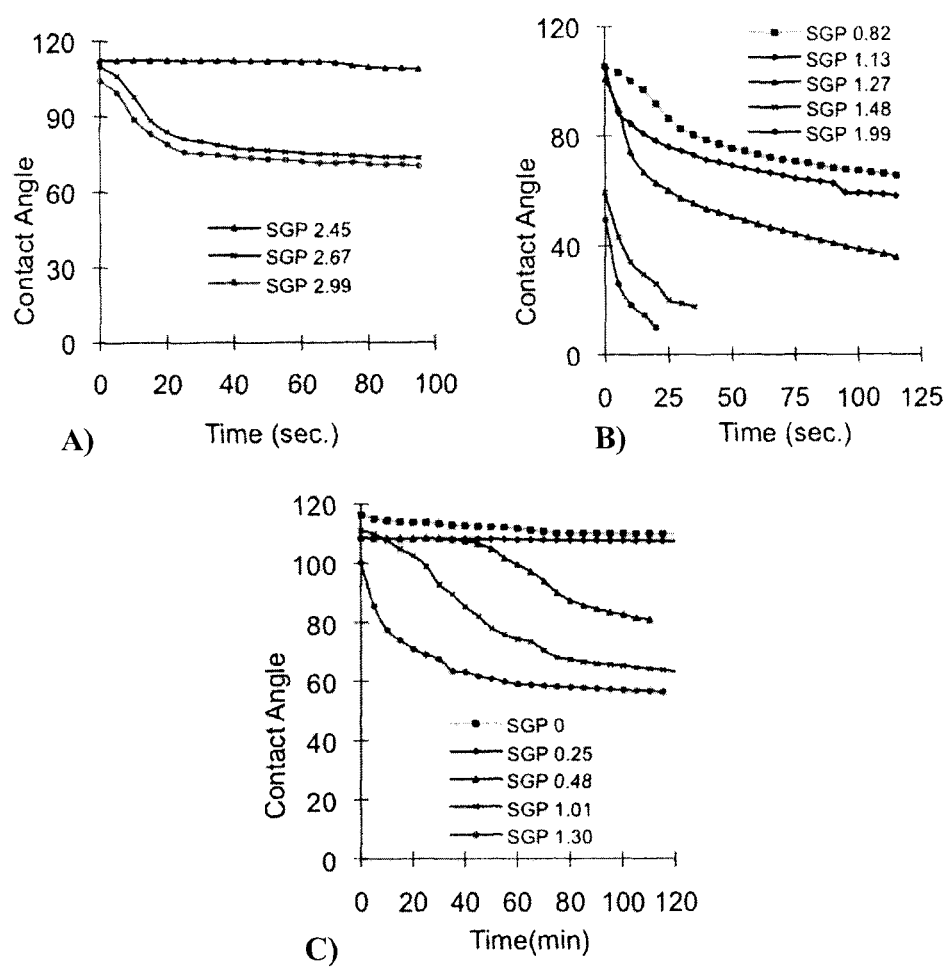

FIG. 6 contains graphs showing water contact angles decreasing in proportion with time on APS-modified PDMS containing (a) 5% DC1107, (b) 1% DC1107 and (c) 0.5% DC1107.

Figure 7:
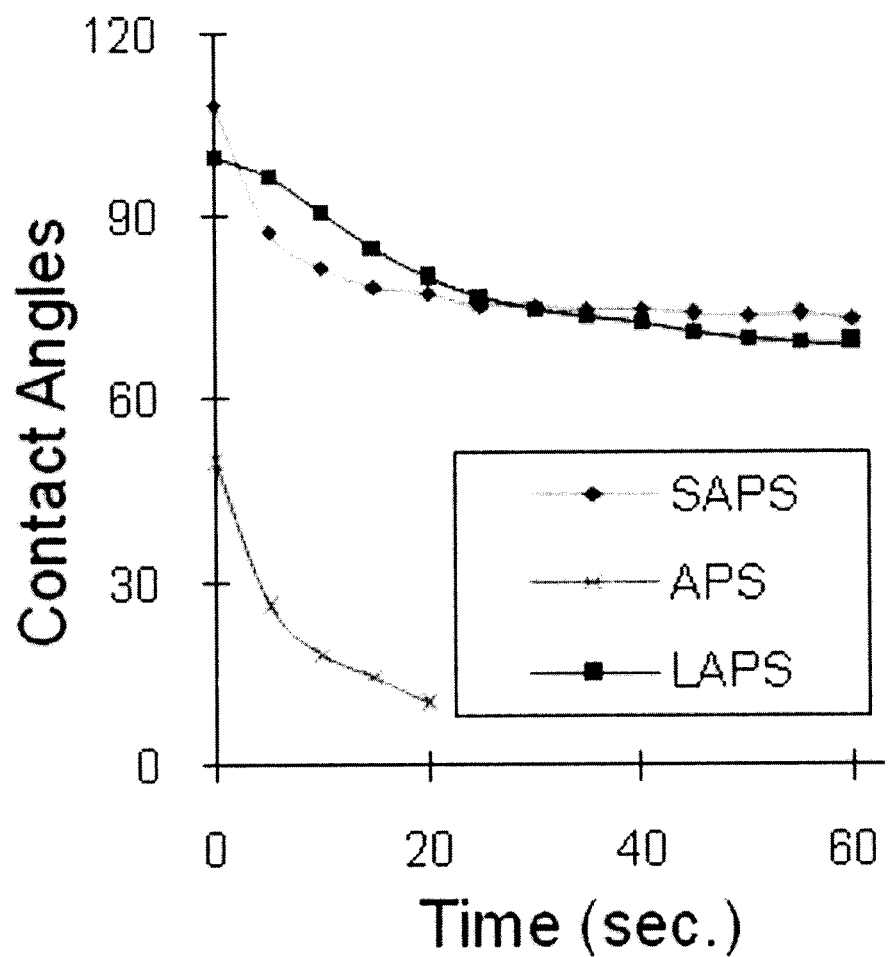

FIG. 7 is a graph showing that water contact angles decrease with time on SiH-modified PDMS elastomers containing 1% DC1107 grafted with SAPS, APS and LAPS, respectively. The grafting percentage of SAPS, APS and LAPS modified PDMS are 18.7%, 14.1% and 17.1%, respectively.

Figure 8:
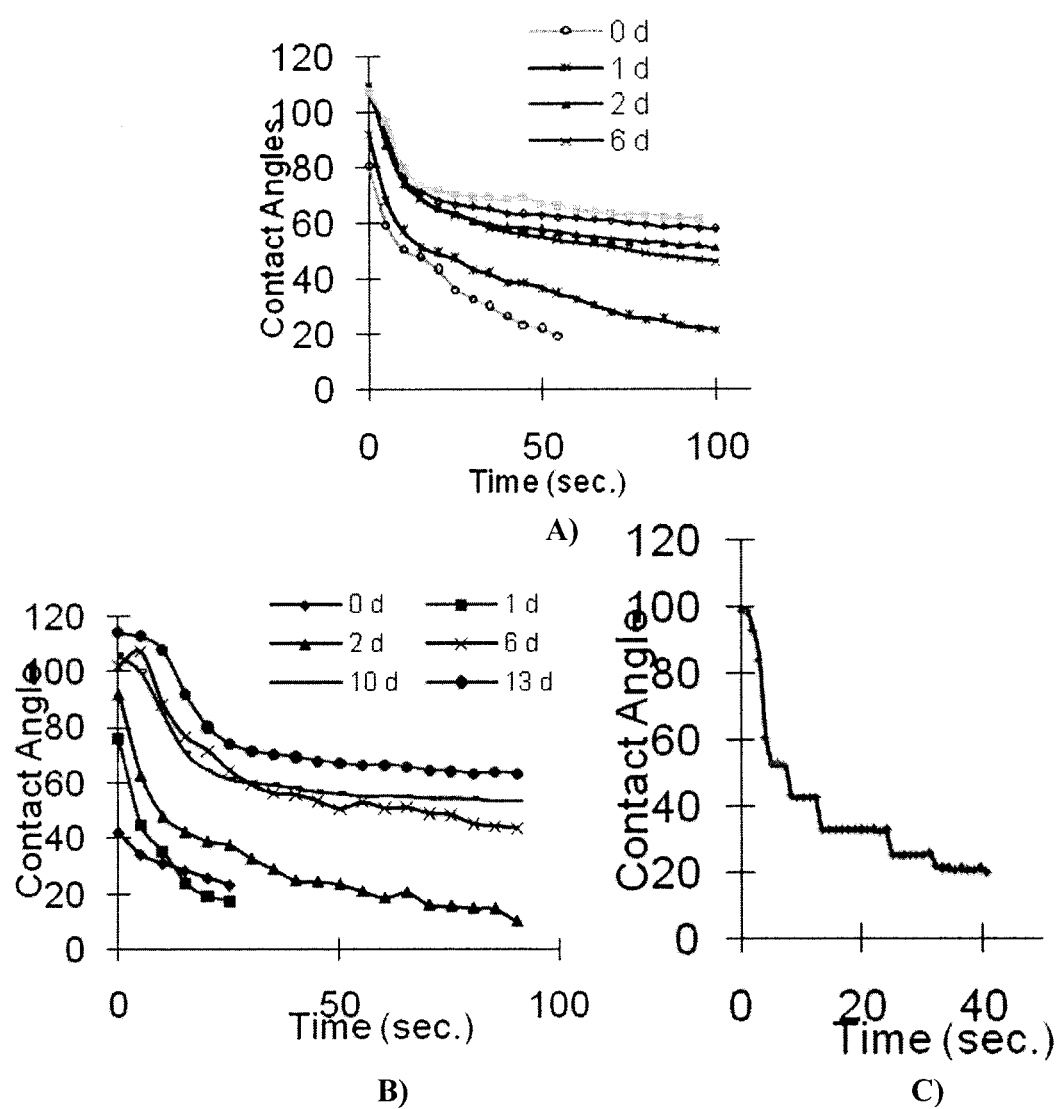

FIG. 8 contains graphs showing the stability tests of APS-modified PDMS samples, which were immersed in (a) pH=10 buffer solution, and (b) pH=4 buffer solution, separately. (c) One APS-modified PDMS sample, whose grafting percentage is 14.1%, was tested after 5 months.

DESCRIPTION OF VARIOUS EMBODIMENTS

(i) Definitions

Unless otherwise indicated, the definitions and embodiments described in this and other sections are intended to be applicable to all embodiments and aspects of the disclosure herein described for which they are suitable as would be understood by a person skilled in the art.

The term "superhydrophilic" as used herein refers to a substrate surface for which the contact angle of a sessile drop of water is <10°.

The term "superwetter" as used herein refers to a compound that can render surfaces superhydrophilic.

The term "siloxane" as used herein refers to a functional group comprised of units of the formula "$R^1R^2SiO$", wherein $R^1$ and $R^2$ are, independently, an alkyl, alkenyl or aryl group. When R is methyl, the group is referred to herein as a "methylsiloxane".

The term "alkyl" as used herein refers to straight or branched chain alkyl groups containing 1, 2, 3, 4, 5 or 6 carbon atoms.

The term "alkenyl" as used herein refers to straight or branched chain alkenyl groups containing 1, 2, 3, 4, 5 or 6 carbon atoms.

The term "aryl" as used herein refers to aromatic carbocyclic rings having at least one phenyl ring containing 6, 7, 8, 9 or 10 carbon atoms and that is unsubstituted or substituted with 1, 2, 3, 4, 5 or 6 alkyl groups (each independently selected).

As used in this application, the singular forms "a", "an" and "the" include plural references unless the content clearly dictates otherwise. For example, an embodiment including "a compound" should be understood to present certain aspects with one compound or two or more additional compound.

In embodiments comprising an "additional" or "second" component, the second component as used herein is chemically different from the other components or first component. A "third" component is different from the other, first, and second components, and further enumerated or "additional" components are similarly different.

The term "suitable" as used herein means that the selection of the particular conditions would depend on the specific method to be performed, but the selection would be well within the skill of a person trained in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(ii) Compounds of the Disclosure

Silicone elastomers are exceptionally hydrophobic substrates. Surface modification by oxidation or grafting of hydrophilic polymers often fails to give hydrophilic surfaces because silicone chains within the elastomer migrate past the hydrophilic modification to 'revert' to a hydrophobic surface. It has been demonstrated herein that an allyl-functionalized surface modifier, APS, comprised of a poly(ethylene glycol) (PEG) chain modified at one end by an allyl group and at the other by a siloxane can be grafted to substrates, such as silicone elastomer surfaces. The resulting surfaces were completely and rapidly wetted by water. The spreading rate of water droplets (0.02 ml water) across an APS-modified silicone elastomer surface was 1 mm s$^{-1}$ for the first 3 seconds: the contact angle decreased to below 10° within about 1 minute with droplet spreading to about 15 times the original size. The surface remained superhydrophilic for at least 5 months during storage in air, although the rate of spreading decreased over time.

Accordingly, the present disclosure includes a compound of the formula (I):

$$\diagup\!\!\!\!\diagdown\diagdown_\text{O}\diagdown\diagup\diagdown_\text{O}\bigl[\text{O}\diagdown\diagup\bigr]_n\text{O}\diagdown\diagup\text{(-)}_m R^1 \quad (I)$$

wherein
n is 6, 7, 8, 9 or 10;
m is 1, 2, 3, 4, 5 or 6; and
$R^1$ is a straight or branched chain siloxane.

In an embodiment of the application, n is 7, 8 or 9. In a further embodiment, n is 8.

In an embodiment of the application, m is 1, 3, 4, 5 or 6. In a further embodiment, m is 1, 3, 4 or 5. In yet another embodiment, m is 1 or 3.

In an embodiment of the application $R^1$ is a siloxane comprising from 2 to 15 silicon atoms. In a further embodiment, all $R^1$ is a methylsiloxane. In another embodiment, the $R^1$ is branched trisiloxane (containing 3 silicon atoms). In yet another embodiment, $R^1$ is selected from one of the following groups:

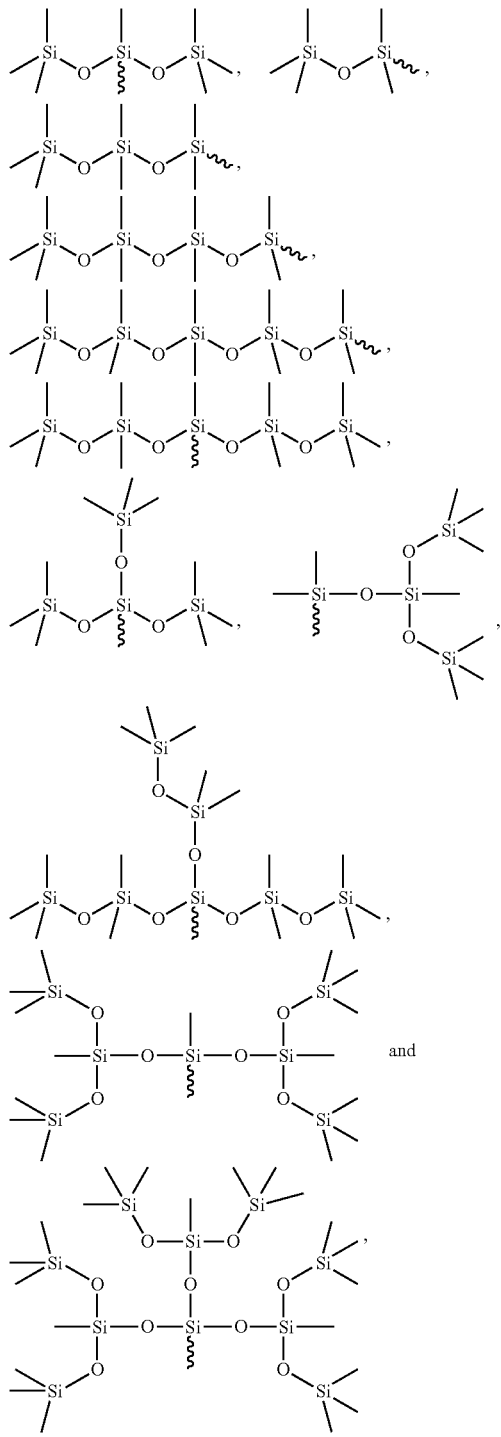

wherein ∿∿ represents the point of attachment of the group to the compound for Formula (I). In another embodiment the siloxane is

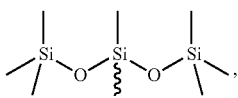

wherein ∿∿ represents the point of attachment of the group to the compound for Formula (I).

(iii) Methods and Uses of the Disclosure

The allyl-functionalized compounds of Formula (I), comprised of a poly(ethylene glycol) (PEG) chain modified at one end by an allyl group and at the other by siloxane, can be grafted to substrate surfaces. For example, a silicone elastomer surface grafted with a compound of Formula (I) comprising ethylene glycol chains of about 8 ethylene oxide (EO) monomer units and a branched trisiloxane, led to silicone surfaces that were completely and rapidly wetted by water. The spreading rate of water droplets (0.02 ml water) across this modified silicone elastomer surface was 1 mm s$^{-1}$ for the first 3 seconds and the contact angle decreased to below 10° within about 1 minute with droplet spreading to about 15 times the original size. The surface remained superhydrophilic for at least 5 months during storage in air, although the rate of spreading decreased over time.

Accordingly, the present disclosure includes a method of modifying a surface of a substrate comprising grafting one or more compounds of Formula (I) to the substrate. In an embodiment, the grafting is done by reacting the substrate and the one or more compounds of Formula (I) as defined above under conditions to form a covalent attachment therebetween. In an embodiment, the covalent attachment is formed by a reaction between the allyl group on the one or more compounds of Formula (I) and one or more functional groups on the substrate.

In an embodiment, the substrate is one that can be made to react with the one or more compounds of Formula (I). In an embodiment, the substrate is poly(dimethylsiloxane) (PDMS), polystyrene (PS), polypropylene (PP), polyethylene, poly(methyl methacrylate) (PMMA) or related acrylic polymers, polycarbonate (PC), polyisopropylene (PI), nylon or related polyamides, polyacylamides, fluorocarbons or mixtures thereof. A person skilled in the art would know how to modify the surfaces of such polymers so that they react with the allyl group of Formula I to form a covalent linkage. For example, when the substrate is a silicone polymer (such as PDMS) comprising Si—H functional groups the compound of Formula (I) is reacted with the surface of the substrate under hydrosilylation reaction conditions. In an embodiment, the hydrosilylation reaction conditions comprise a catalyst, for example a noble metal catalyst, most generally a platinum complex, such as Karstedt's catalyst. In a further embodiment, the hydrosilylation conditions comprise dissolving the one or more compounds of Formula (I) is a suitable solvent and adding the catalyst. The substrate to be surface modified is then immersed in the solution of the one or more compounds of Formula (I) and catalyst and allowed to react at suitable temperature and time. After the grafting reaction, the modified substrates can be washed and dried.

The degree of hydrophilicity can be manipulated by controlling the density of superwetting agents (compounds of Formula (I)) that are grafted to the surface. The density can be increased by either increasing the concentration of compounds of Formula (I) in the reaction mixture used to chemically modify the surface and/or increase the reaction time.

Methods of creating Si—H functional surfaces on silicone polymers are known.[16, 33] In an embodiment, the SiH containing silicone polymers are prepared using a 10:1:1 silicone elastomer:curing agent:(HMeSiO)$_n$ which incorporates the excess SiH-containing polymer into the prepolymer.

The present disclosure also includes a use of one or more compounds of Formula (I) to modify a surface of a substrate.

The present disclosure also includes a substrate that has been surface modified by grafting of one or more compounds of Formula (I), as defined above, onto its surface. In an embodiment, the substrate is PDMS. In an embodiment, the substrate has been surface modified to have a water contact angle of 10° or less.

EXAMPLES

The following Examples are set forth to aid in the understanding of the invention, and are not intended and should not be construed to limit in any way the invention set forth in the claims which follow thereafter.

Materials

Poly(ethylene glycol) (PEG, Mn=400, 1000), tetraglyme, sodium hydride (60 wt % in oil), allyl bromide, tetrahydrofuran (THF) and Karstedt's platinum catalyst (platinum(0)-1,3-divinyl-1,1,3,3-tetramethyldisiloxane complex solution) were purchased from Sigma-Aldrich Inc. Monoallyl-PEG-OH A250 (Mn=250), A350 (Mn=350) and A550 (Mn=550) were gifts from Clariant Corporation. Bis(trimethylsiloxy)methylsilane (Bis-H) was obtained from Gelest Inc. The Sylgard 184 silicone elastomer kit, containing the PDMS oligomers and curing agent, and poly(hydromethylsiloxane) (DC1107, PHMS) were purchased from Dow Corning. THF was dried over activated alumina before use; otherwise, compounds were used as received.

Characterization $^1$H NMR and $^{13}$C NMR spectra were obtained on Bruker AC-200 (200-MHz) spectrometer. The molecular weight and mass spectra were determined on a Micromass Global Q-TOF Ultima (MALDI/CapLC-ESI Quadrupole Time of Flight) Mass Spectrometer. ATR-FTIR spectra were obtained on Bio-Rad FTS-40 (Fourier transform IR) spectrometer with an ATR accessory, on which a 45° rectangle ZnSe crystal was used. Surface water contact angle and surface tension were recorded using a Krüss V1.50 drop shape analyzer.

Synthetic Procedures

Example 1

Synthesis of Diallyl-Terminated PEO (DAP) (Details for 400 MW PEG)

PEG (8.0 g, 0.02 mol) was dissolved in anhydrous THF to give a 20 wt % solution, into which excess sodium hydride (2.0 g, 0.05 mol) was added slowly over 30 min. Allyl bromide (4.8 g, 0.04 mol) was then added dropwise into the solution. The mixture was allowed to react with stirring for 16 h under nitrogen atmosphere. Afterwards, the mixture was filtered through a Celite column and the filtrate was evaporated. The resulting yellow oil (8.2 g) was obtained in a yield of 85%. Alternatively, diallyl tetraglyme SDAP (shorter DAP) was formed in 89% yield (8.2 g) from tetraglyme and diallyl PEG 1000 and LDAP (longer DAP) in 70% yield (8.0 g) from PEG 1000 using similar processes.

DAP $^1$H NMR (200 MHz; CDCl$_3$) δ: 5.94-5.77 (m, 2H, =CH—), 5.27-5.10 (m, 4H, CH$_2$=), 3.98 (d, 4H, J=5.6 Hz, —O—CH$_2$allyl), 3.61-3.52 (m, 38H, CH$_2$—O). $^{13}$C NMR (200 MHz, CDCl$_3$) δ: 134.7, 117.0, 72.2, 70.5.

SDAP $^1$H NMR (200 MHz; CDCl$_3$) δ: 5.86-5.75 (m, 2H, =CH—), 5.24-5.08 (m, 4H, CH$_2$=), 3.95 (d, 4H, J=5.6 Hz, —O—CH$_2$allyl), 3.59-3.51 (m, 18H, CH$_2$—O). $^{13}$C NMR (200 MHz, CDCl$_3$) δ: 134.8, 117.1, 72.3, 70.6.

LDAP ($^1$H NMR (200 MHz; CDCl$_3$) δ: 5.98-5.80 (m, 2H, =CH—), 5.28-5.12 (m, 4H, CH$_2$=), 3.98 (d, 4H, J=5.6 Hz, —O—CH$_2$allyl), 3.75-3.62 (m, 86H, CH$_2$—O). $^{13}$C NMR (200 MHz, CDCl$_3$) δ: 134.7, 117.0, 72.2, 70.5.

Example 2

Synthesis of Allyl PEO Siloxane (APS) (Details for PEG 400 MW)

DAP (2.0 g, 0.004 mol) was dissolved in anhydrous toluene (10 ml), into which Bis-H (0.89 g, 0.004 mol) in toluene (25 ml) was added along with Karstedt's catalyst (0.02 ml). The solution was stirred under Ar for 24 h at room temperature. Afterwards, the solution was evaporated and yellow oil was obtained in a yield of 80% (2.3 g). Analogous processes with the shorter and longer diallyl-PEG derivatives led to SAPS in 80% yield (2.5 g) and LAPS in 45% yield (2.2 g), respectively.

APS (note that the actual DP of the starting PEG was ~9.5. The data is normalized to 9.0 for convenience) $^1$H NMR (200 MHz; CDCl$_3$) δ: 5.92-5.83 (m, 1H, =CH—), 5.30-5.14 (m, 2H, CH$_2$=), 4.01 (d, 2H, J=5.6 Hz, —O—CH$_2$CH=CH$_2$), 3.63-3.58 (m, 36H, —O—CH$_2$ether), 3.39 (t, 2H, J=7.2 Hz, O—CH$_2$), 1.62-1.51 (m, 2H, —CH$_2$—CH$_2$—Si), 0.45-0.37 (m, 2H, —CH$_2$—Si), 0.06 (s, 18H, TMSO), 0.01 (s, 3H, CH$_3$—Si). $^{13}$C NMR (200 MHz, CDCl$_3$) δ: 134.8, 117.2, 74.2, 72.4, 70.0, 23.2, 13.5, 1.9, −0.3. IR, see FIG. 1. HRMS (ESI) m/z calcd for [C$_{29}$H$_{64}$O$_{11}$Si$_3$+NH$_4$]$^+$ 690.4083. found 690.4100.

SAPS $^1$H NMR (200 MHz; CDCl$_3$) δ: 5.96-5.83 (m, 1H, =CH—), 5.30-5.1 (m, 2H, CH$_2$=), 4.01 (d, 2H, J=5.4 Hz, —O—CH$_2$CH=CH$_2$), 3.65-3.58 (m, 18H, —O—CH$_2$ether), 3.39 (t, 2H, J=7.2 Hz, O—CH$_2$), 1.62-1.51 (m, 2H, —CH$_2$—CH$_2$—Si), 0.45-0.37 (m, 2H, —CH$_2$—Si), 0.06 (s, 18H, TMSO), 0.01 (s, 3H, CH$_3$—Si). $^{13}$C NMR (200 MHz, CDCl$_3$) δ: 134.8, 117.2, 74.2, 72.3, 70.0, 23.2, 13.5, 1.9, −0.3.

The LAPS compound was a produced as a mixture of monosilyl (LAPS) and disilyl species in an approximately 2:1 ratio. For clarity, the spectra of the two compounds are reported separately. LAPS $^1$H NMR (200 MHz; CDCl$_3$) δ: 5.98-5.79 (m, 1H, =CH—), 5.28-5.12 (m, 2H, CH$_2$=), 4.00 (d, 2H, J=5.6 Hz, —O—CH$_2$CH=CH$_2$), 3.65-3.58 (m, 86H, —O—CH$_2$ether), 3.39 (t, 2H, J=7.2 Hz, O—CH$_2$), 1.62-1.51 (m, 2H, —CH$_2$—CH$_2$—Si), 0.45-0.37 (m, 2H, —CH$_2$—Si), 0.06 (s, 18H, TMSO), 0.01 (s, 3H, CH$_3$—Si). The bis-silylated analogue: $^1$H NMR (200 MHz; CDCl$_3$) δ: 3.65-3.58 (m, 86H, —O—CH$_2$ether), 3.39 (t, 2H, J=7.2 Hz, O—CH$_2$), 1.62-1.51 (m, 2H, —CH$_2$—CH$_2$—Si), 0.45-0.37 (m, 2H, —CH$_2$—Si), 0.06 (s, 36H, TMSO), 0.01 (s, 6H, CH$_3$—Si). $^{13}$C NMR (200 MHz, CDCl$_3$) δ: 134.8, 117.2, 74.2, 72.3, 70.0, 23.2, 13.5, 1.9, −0.3.

Example 3

Synthesis of bis-heptamethyltrisiloxanyl-PEG (SiPS)

DAP (4.0 g, 0.17 mol) was dissolved in anhydrous toluene (10 ml), into which Bis-H (4.0 g, 0.34 mol) in dry THF (25 ml) was added along with Karstedt's catalyst (0.02 ml). The solution was stirred under Ar for 24 h at room temperature. Afterwards, the solution was evaporated and a yellow oil was obtained in a yield of 88% (7.3 g). $^1$H and $^{13}$C NMR shows that a mixture of regioisomers resulted from the hydrosilylation in a ratio of $RCH_2CH_2CH_2Si:RCH_2CHSiCH_3$ of ~1:1.

SIPS $^1$H NMR (200 MHz; CDCl$_3$) δ: 3.59 (s, 36H), 3.36 (t, 4H, J=6.8 Hz), 1.56-1.51 (m, 4H), 0.86 (t, CH$_3$, J=5.2 Hz, 1.5H), 0.38 (m, CH$_2$+CH 1.5H), 0.06 (s, OTMS, 18H), 0.03 (s, 18H), −0.05 (s, 6H). $^{13}$C NMR (200 MHz, CDCl$_3$) δ: 74.2, 73.1, 72.3, 70.62, 25.6, 23.2, 13.5, 10.8, 2.0, 1.9, −0.3.

Example 4

Si—H Functional Silicone Elastomers

The Sylgard PDMS oligomer (5.0 g) and curing agent (0.5 g) were mixed together in a weight ratio of 10:1 along with additional PHMS (DC1107), where 0.25 g, 0.05 g and 0.025 g, respectively, were used to give formulations with 5 wt %, 1 wt % and 0.5 wt % PHMS. The mixtures were poured into a Petri dish, degassed and cured under vacuum for 24 h. The cured PDMS samples were cut into small sample coupons with average diameter of 15 mm, and a thickness of 3 mm. The samples were swollen for an hour in dry THF (20 ml) to remove the ungrafted compounds. After repeating this step three times, the elastomers were dried to constant weight under vacuum.

Example 5

Surface Grafting of APS and Other Mono-allylPEG Compounds on PDMS

A series of APS solutions of various concentrations in THF, respectively, were mixed with Karstedt's Pt catalyst (0.01 ml in 10 ml THF). The small PDMS sample coupons were placed into the above solutions for 12 h at 50° C. The samples were swollen for 1 h, washed with THF (3×20 ml), and dried in a vacuum oven (~10 Torr) at room temperature to constant weight. The surface grafting percentage of APS was calculated: Surface Grafting Percentage %=100*(W1−W0)/A*W0, where W1 is the weight of PDMS after grafting APS, W0 is the weight of the PDMS elastomer before grafting and A is the surface area of PDMS elastomers (7.07 cm2) (see Table 1).

Surface grafting of monoallyl PEG A250, A350, A550 and diallyl PEG followed the same procedures.

Example 6

Wetting Behavior

The ability of solutions of APS and related compounds to wet substrates was established using a drop shape analyzer. The contact angles and total spreading were established immediately after placing an aqueous drop volume ~0.02 ml onto the surface of polystyrene (a new Petri dish) or a cleaned glass slide.

The ability of water to wet out a variety of surface modified silicones was also established using the drop shape analyzer. These data include initial and final contact angles, and total spreading area for: PEG-modified silicones (FIG. 6, FIG. 7, Table 1); water contact angles of APS-modified PDMS (SGP 14 wt %) were measured each month for a period of 5 months (2 min. each time) for each month; APS-modified PDMS coupons after soaking in pH 4 and pH 10 buffer solutions, respectively (1, 2, 6, 10, 13 days). Prior to each test, the coupons were thoroughly washed by DI water (FIG. 8).

Results

Silicone superwetters are generally comprised of a trisiloxane head group, to the central silicon of which is attached an oligo(ethylene oxide) or mixed oligo(ethylene oxide/propylene oxide) chain, through a propyl spacer. Subtle differences in surface activity result from differences in chain length, balance of EO/PO and the nature of the end group R.

Tethering the superwetter to a silicone elastomer surface required a functional group linker on the PEG. Hydrosilylation was chosen as an efficient coupling process commonly employed in silicone synthesis,[31] to cure the elastomers, to create a superwetting silicone, and to tether the superwetter to the surface. Therefore, an allyl functional superwetter was prepared (APS, SAPS, LAPS) and then grafted to an Si—H functional silicone elastomer surface.

Preparation of the Superwetter APS

Diallyl PEG was prepared by standard Williamson synthesis starting from HO-terminated PEG and allyl bromide, in the presence of NaH. The process is facile with low molecular weight PEGs, although the separation of pure diallyl PEG from the monoallyl PEG or starting material becomes increasingly difficult with increasing molecular weight. Such problems do not arise below a molecular weight of about 500: use of excess reagent led to complete conversion of PEG-OH to diallyl PEG. Compounds derived from PEGs of three different molecular weights were prepared: DAP (MW 494), SDAP (MW 274) and LDAP (MW 1066). Note that DAP and LDAP were prepared from PEG nominally of MW 400 (DP 9) and 1000 (DP 22), but the actual degrees of polymerization were about 9.4 and 21.8, respectively. The nominal values of DP 9 and DP 22 are used for convenience in reporting spectral data.

Figure 1:
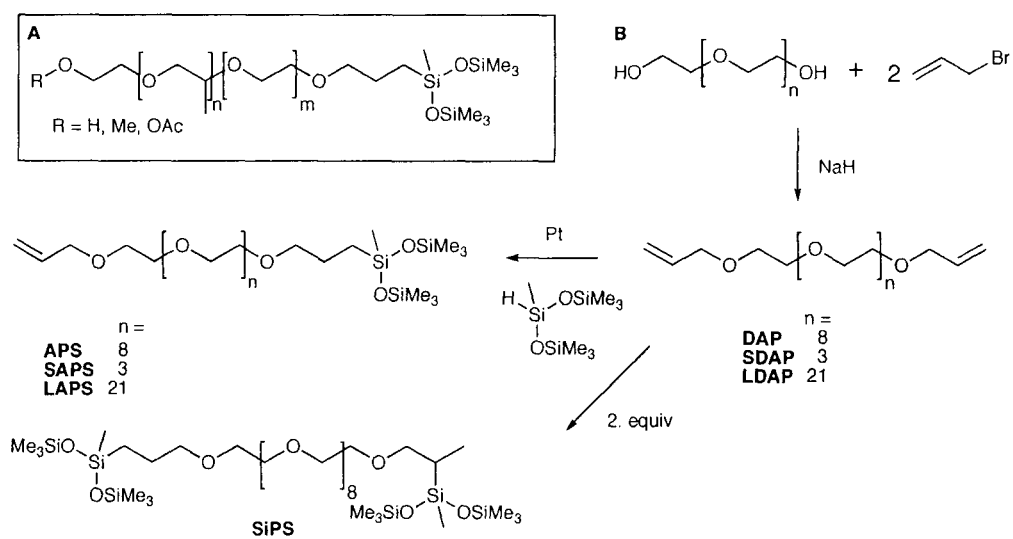
FIG. 1 shows (a) structures of prior art superwetters; and (b) synthesis and structures of diallyl PEG; monosilyl and monoallyl PEG and bissilyl PEG.

The synthesis of the functional superwetter APS, and the analogues of lower SAPS and higher molecular weight LAPS, rely on partial hydrosilylation of diallyl PEG with Bis-H (FIG. 1). Statistical mixtures are frequently problematic when monofunctionalization of a difunctional material is attempted. In the case of LAPS, an inseparable mixture comprised of approximately a 2:1 mixture of mono and bissilylated material was formed. However, only the mono-allyl LAPS can bind to the silicone surface. In the case of APS, the NMR data did not permit an explicit assessment of the relative amount of diallyl-PEG starting material, bis-silylated PEG and the desired allyl/silyl PEG: the product showed perfect integration for a monoallyl, monosilyl PEG. Therefore, the surface activity of the APS was independently established by comparison with the precursor DAP and putative byproduct SiPS. As shown below in more detail, this analysis demonstrated that the synthesized APS was clearly distinct from both DAP and SiPS.

Figure 2:
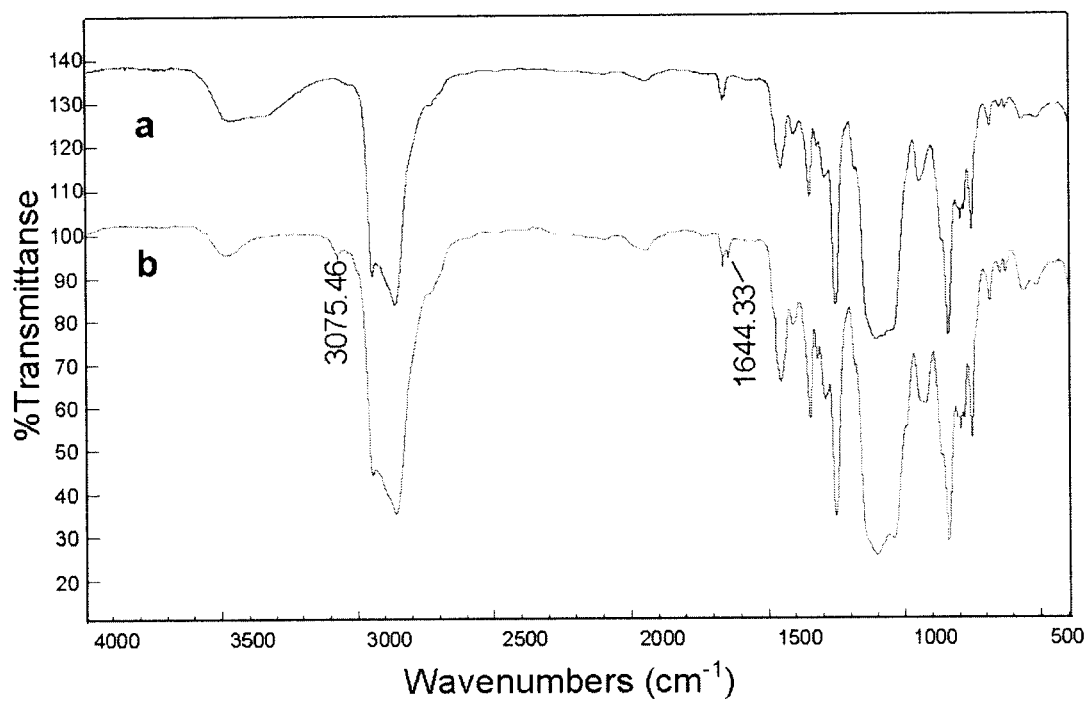
FIG. 2 shows the FT-IR spectra of (a) Dow Corning Q2-5211 and (b) APS.

The similarity of APS to a commercial superwetter and Dow Corning Q2-5211 (R═H in FIG. 1), can be seen from their FT-IR spectra (FIG. 2). However, the band at 3075 cm$^{-1}$ belongs to the stretching vibration of ═C—H, and at 1644 cm$^{-1}$ belongs to the stretching vibration of C═C, data consistent with the presence of an allyl group APS.

Figure 3:
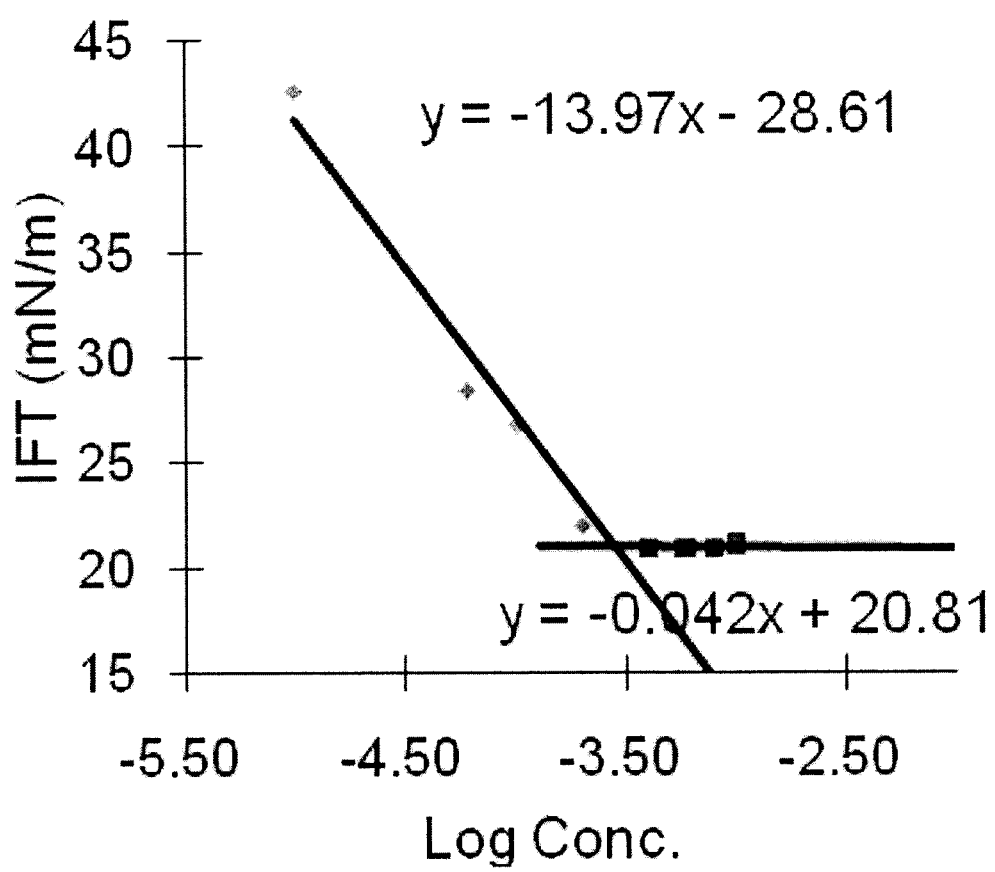
FIG. 3 is a graph showing the determination of cac for APS at 22° C.

The solubility of APS was established by measuring the cac (critical aggregation concentration), and was calculated to be 0.28 g l$^{-1}$ (FIG. 3), a value that is similar to commercial superwetters.

Wetting Performance

The ability of APS to disperse an aqueous phosphate buffer solution (pH=7) was determined on both hydrophobic (polystyrene) and hydrophilic (glass) surfaces. As a control, a 5 μl drop of buffer without surfactant was shown to have an area of 0.50 cm² on glass and just 0.031 cm² on polystyrene. Additional controls with 0.1 wt % (0.2 wt %, 0.5 wt %) DAP and 0.1 wt % (0.2 wt %, 0.5 wt %) SiPS, respectively, had only marginally larger surface areas on either glass or polystyrene. Thus, neither of these materials shows effective wetting behavior. By contrast, when 1.5 wt % APS was included in the buffer, the maximum wetting diameter area on polystyrene was close to 6.16 cm², close to 200 times the area of the original buffer solution. Thus, APS has characteristics of typical superwetters.

Having prepared a functional superwetter, attention was turned to grafting the material to a polymer surface, in this case a silicone elastomer. To do so, Si—H functional surfaces that would undergo hydrosilylation with APS were first created. A variety of strategies have been developed that lead to the Si—H silicone elastomers, including post-cure surface modification.[16, 33] In this work, an alternative and straightforward strategy was chosen in which excess SiH-containing polymer was incorporated in the Sylgard prepolymer:[34] rather than 10:1 polymer/curing agent, the elastomers were prepared from 10:1:1 polymer:curing agent:$(HMeSiO)_n$ (Dow Corning 1107). The excess SiH is thus present both within the cured elastomer and on the external surface.

Elastomers based on these starting materials were SiH rich at the interface, as shown by FTIR. The intense SiH peak at 2157 cm$^{-1}$ in the IR of the elastomers disappeared after PDMS was modified by APS using platinum-catalyzed hydrosilylation (FIG. 1): the peaks at 2863 cm$^{-1}$ confirmed the presence of PEO on the silicone surface.[35] However, in addition to surface modification, it is clear that this process also leads to loss of some SiH contained within the silicone elastomer.

Figure 4:
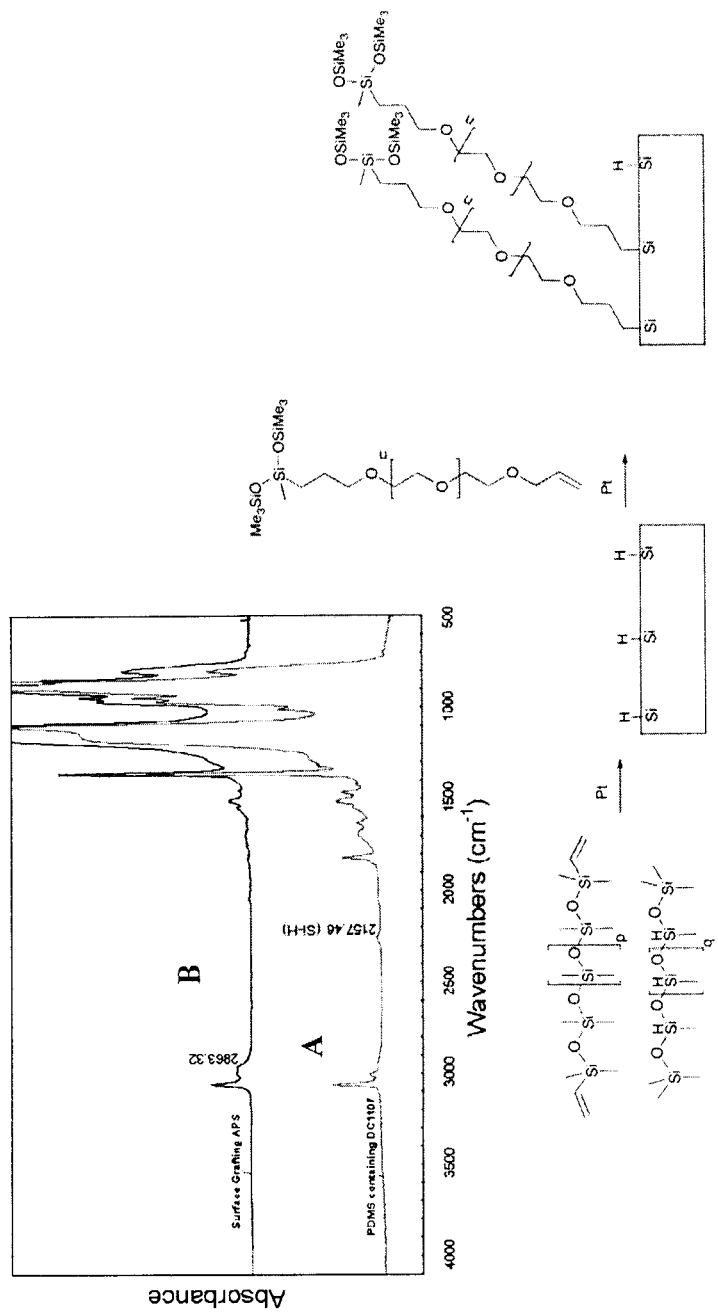
FIG. 4 shows a schematic of the modification of silicone elastomers with APS as well as the ATR-FTIR spectra of PDMS A: before, and B. after surface grafting with APS (inset—SiH region).

As discussed above, the synthesis of the functional superwetter APS relies on partial hydrosilylation of diallyl PEG with Bis-H (FIG. 4). Surface activity showed that neither the diallyl (DAP) or disiloxane-modified PEG compounds (SiPS) exhibited any superwetting ability at all on their own in aqueous solutions. The latter compound cannot bind by hydrosilylation to the surface. In a control experiment, pure DAP was grafted to the PDMS elastomer using various concentrations in THF (10, 20, 50%). The lowest contact angle of the materials prepared was 80°. Thus, the superwetting described in more detail below can be ascribed to Silicone-APS modification only, and not a consequence of DAP binding. It further reinforces the contention above that the APS was major product in the hydrosilylation of the silicone surface: DAP or DAP-modified surfaces do not have superwetting properties, while APS and APS-modified surfaces clearly do.

Figure 5:
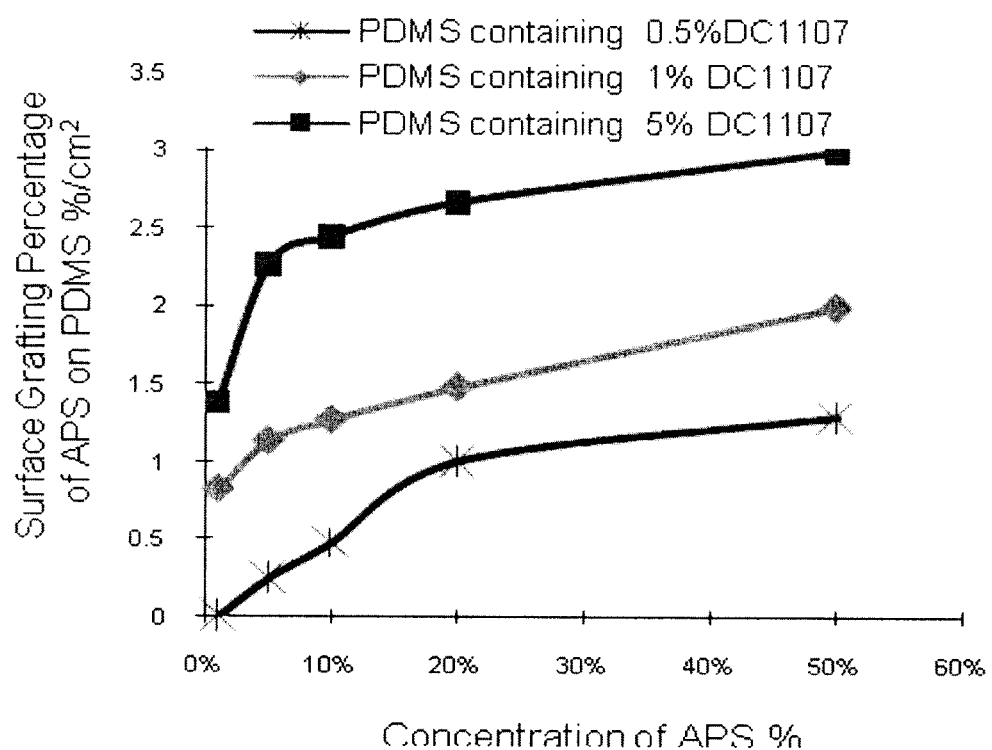
FIG. 5 is a graph showing the grafting percentage of APS on PDMS. The surface hydrosilylation was done during 12 h.

Small quantities of surface-active materials can have an extraordinary impact on the wetting behavior of surfaces. To ensure that the surface behavior of these silicone elastomers was not affected by any residual, unreacted APS, the surface-modified silicones were extensively swollen and washed first by THF, and then by $CDCl_3$ to remove any physically absorbed compounds. The 200 MHz $^1H$ NMR spectrum of the washed, modified elastomer showed the presence of the APS propylene linker at $\delta$=0.468-0.383,[36] while peaks at $\delta$=3.65-3.60 are consistent with the presence of PEO (no residual alkene groups from APS were observed). The surface density of grafted APS is a consequence of the availability of SiH groups on the elastomer surface and of the concentration of APS used in the modification process: the correlation of grafting efficacy to these two parameters is shown in FIG. 5. The grafting that occurred has its main locus at the external interface. PEO is almost insoluble in silicone polymers, and when incorporated internally, leads to hazy→white elastomers.[37, 38] The elastomers produced here were optically transparent.

Superwetters received their designation because aqueous solutions containing them spread both extensively and rapidly. As noted above, the cac of APS is approximately 0.28 g l$^{-1}$ (FIG. 5). At concentrations (well) above the cac, spreading of APS-containing aqueous solutions is both fast and effective: one drop of 1 wt % APS aqueous solution increased in area from 0.03 cm² to 4.91 cm² in just 5 seconds (data not shown).

Contact angle measurements using distilled water were made on the APS-grafted silicone surfaces. There was an expected correlation between the degree of APS incorporation on the surface and the water contact angle. The degree to which the contact angle dropped with APS incorporation was extremely unusual. In some cases, the contact angle dropped to nearly zero within one minute. This is very surprising because PEG-modified silicone surfaces typically have contact angles of about 65-80°, although lower values have been reported (see below). This effect is highly dependent on surface coverage: at very high coverage (high concentration of APS during grafting, high concentration of SiH in the elastomers), or very low coverage (low concentration of APS during grafting and/or low concentration of SiH in the elastomers) much higher contact angles were observed. These differences are reflected in the surface grafting percentage (SGP, see experimental section—essentially a weight gain/surface area): larger values imply higher surface concentrations of APS.

The facile wetting of APS-tethered silicone surfaces was not a consequence alone of the presence of PEG on the surface. To demonstrate this, monoallyl PEGs of three different molecular weights: A250 (~$EO_5$); A350 (~$EO_7$) and A550 (~$EO_{12}$), respectively, were grafted onto PDMS elastomers that contained 1 wt & DC1107[39-41] using the same procedure as for APS. On none of the PEG-modified surfaces was superwetting behavior observed. As shown in Table 1, neither was grafting as efficient nor were contact angles lowered as much by any of the EO materials as by APS. The lowest water contact angles reported on PEG-modified surfaces is about 20°[42-45] although experience suggests the number is normally much higher, significantly higher than the case with APS.

In solution, the chemical structure of the trisiloxane surfactants influences the spreading behavior. Silicone surfactants, although typically not superwetters, frequently use copolymers of poly(propylene oxide) (PPO) and PEO as the hydrophilic component.[46] Compared with propylene oxide (PO), EO is more hydrophilic and more suitable as the hydrophilic part of trisiloxane superwetter.[47, 48] Therefore, tethered PPO derivatives were not examined. However, the surface activity of superwetters is also affected by EO chain length: the optimal spreading effect of superwetting surfactants is observed when the number of repeat units (EO) is about 6-8,[49] longer or shorter lengths of EO chains will decrease the spreading area. To examine the role of EO chain length on surfaces modified with tethered superwetters, two compounds with similar structures to APS were synthesized and grafted to the surface of PDMS elastomers: SAPS has a very short EO tether $(EO)_4$, while the other, LAPS, has longer EO chain $(EO)_{22}$ (FIG. 1). At comparable surface coverage, neither surfaces modified with the shorter or longer PEG surfactants, SAPS and LAPS, respectively, could achieve the same low contact angles or same high, rapidly attained, surface coverage as APS (FIG. 7, Table 1).

The magnitude of spreading of APS in water was examined, and water on APS tethered to silicone, but not yet considered is the rate of spreading: rapid rates of spreading are also emblematic of superwetters. The water spreading rate on APS-modified PDMS was calculated according to a literature method[26] where:

$$\text{spreading rate} = dD/dt \quad (1)$$

and, $$\text{spreading area} = d\Delta S/dt, \quad (2)$$

wherein D is the diameter of water droplet, S is the surface area covered by water and t is the spreading time. A series of experiments demonstrated that aqueous solutions of APS spread to approximately the same degree and at a similar velocity to the commercial superwetter L77. That is, replacing a terminal alcohol, acetate, etc., on the PEG block with an allyl group leads only to subtle changes in wetting properties. The situation is quite different when the superwetter is tethered.

While water spread readily on tethered APS surfaces, it did so to a lower degree and at a lower rate than when the surfactant was free in solution. In addition, the spreading behavior was quite different. While an aqueous solution of APS spread rapidly at an approximately linear rate across a surface, there were two stages for water spreading on the freshly prepared APS-modified surface. In the case of the sample of PDMS made with 1 wt % DC1107 and grafted with 14.7 wt % APS, a 0.02 ml water droplet spread on the surface at a rate of ~1 mm s$^{-1}$ for the first 3 seconds. The water spreading area increased 8 times during this period. Then, the rate decreased to approximately 0.1 mm s$^{-1}$ in the subsequent 30 seconds. The final area covered by water was about 15 times larger than the original one droplet size. This contrasts with the degree of spreading described of superwetters, which increase drop area by approximately 50 times.[26] Note, however, that the contact angle at the edge of the spread droplet approaches 0° when the drop ceases to migrate.

The durability and environmental stability of modified surfaces are factors to consider for their use in real applications. While silicones are normally very stable to degradation, provided that the conditions remain near neutrality, branched trisiloxanes are notoriously unstable to hydrolysis.[27] Superwetters are usually added to the agents to be dispersed and then used immediately in pH 7 buffers. It was observed that, like aqueous solutions of commercial surfactants L-77 and Q2-5211, solutions of APS decomposed in water over a few days to a week: previous experience indicates that hydrolysis of one or more Me$_3$SiO groups occurs. However, it was possible that tethering the superwetter to a surface would change the hydrolytic susceptibility.

The hydrolytic stability of APS-modified PDMS elastomers was tested by soaking for extended periods of time in aqueous pH=4 and pH=10 solutions. The results show that both acidic and basic conditions are detrimental to the ability of water to spread on an APS-modified surface, especially after the first week of modification. However, while spreading is impeded after the surface is exposed to such conditions, the water contact angle can still decrease to 20° over 2-3 minutes. The tethered APS is thus more resistant to hydrolytic degradation than APS in solution. Further degradation while soaking the tethered APS in an aqueous solution occurred in the second week, after which no superspreading effect was observed: contact angles decreased only to about 60° over 1-2 minutes.

The shelf-life of the tethered APS was also established by testing spreading behavior monthly over a period of 5 months: samples of APS-modified surfaces were stored without any special protection on the laboratory bench. Subtle changes were observed over time. While the final contact angle (approaching zero) of water droplets was still achieved after 5 months, spreading rates changed appreciably. Rather than two distinct spreading rates, the droplet would spread to a specific radius, stop for several (typically up to 10) seconds and then spread to a new larger radius. This start-stop-start-stop process was repeated up to about 8 times at which point the approximately 0° contact angle was achieved.

FULL CITATIONS FOR DOCUMENTS REFERRED TO IN THE SPECIFICATION

1. He, Q. G.; Liu, Z. C.; Xiao, P. F.; Liang, R. Q.; He, N. Y.; Lu, Z. H., Preparation of hydrophilic poly(dimethylsiloxane) stamps by plasma-induced grafting. *Langmuir* 2003, 19, (17), 6982-6986.
2. Dumbleton, K. A.; Woods, C. A.; Jones, L. W.; Form, D., Comfort and adaptation to silicone hydrogel lenses for daily wear. *Eye & Contact Lens-Science and Clinical Practice* 2008, 34, (4), 215-223.
3. Nichols, J. J.; Sinnott, L. T., Tear film, contact lens, and patient-related factors associated with contact lens-related dry eye. *Investigative Ophthalmology & Visual Science* 2006, 47, (4), 1319-1328.
4. Hollahan, J. R.; Carlson, G. L., Hydroxylation of polymethylsiloxane surfaces by oxidizing plasmas. *J. Appl. Polym. Sci.* 1970, 14, (10), 2499-2508.
5. Morra, M.; Occhiello, E.; Marola, R.; Garbassi, F.; Humphrey, P.; Johnson, D., On the aging of oxygen plasma-treated polydimethylsiloxane surfaces. *J. Colloid Interface Sci.* 1990, 137, (1), 11-24.
6. Chaudhury, M. K.; Whitesides, G. M., Direct Measurement of Interfacial Interactions Between Semisphereical Lenses and Flat Sheets of Poly(dimethylsiloxane) and their Chemical Derivatives. *Langmuir* 1991, 7, (5), 1013-1025.
7. Chaudhury, M. K.; Whitesides, G. M., Correlation between surface free-energy and surface constitution. *Science* 1992, 255, (5049), 1230-1232.
8. Efimenko, K.; Wallace, W. E.; Genzer, J., Surface modification of Sylgard-184 poly(dimethyl siloxane) networks by ultraviolet and ultraviolet/ozone treatment. *J. Colloid Interface Sci.* 2002, 254, (2), 306-315.
9. Genzer, J.; Efimenko, K., Creating long-lived superhydrophobic polymer surfaces through mechanically assembled monolayers. *Science* 2000, 290, (5499), 2130-2133.
10. Hu, S. W.; Ren, X. Q.; Bachman, M.; Sims, C. E.; Li, G. P.; Allbritton, N., Surface modification of poly(dimethylsiloxane) microfluidic devices by ultraviolet polymer grafting. *Anal. Chem.* 2002, 74, (16), 4117-4123.
11. Hillborg, H.; Gedde, U. W., Hydrophobicity recovery of polydimethylsiloxane after exposure to corona discharges. *Polymer* 1998, 39, (10), 1991-1998.
12. Wang, B.; Chen, L.; Abdulali-Kanji, Z.; Horton, J. H.; Oleschuk, R. D., Aging effects on oxidized and amine-modified poly(dimethylsiloxane) surfaces studied with chemical forced titrations: Effects on electroosmotic flow rate in microfluidic channels. *Langmuir* 2003, 19, (23), 9792-9798.
13. Ginn, B. T.; Steinbock, O., Polymer surface modification using microwave-oven-generated plasma. *Langmuir* 2003, 19, (19), 8117-8118.
14. Liu, Y.; Fanguy, J. C.; Bledsoe, J. M.; Henry, C. S., Dynamic coating using polyelectrolyte multilayers for chemical control of electroosmotic flow in capillary electrophoresis microchips. *Anal. Chem.* 2000, 72, (24), 5939-5944.

15. Buch, J. S.; Wang, P. C.; DeVoe, D. L.; Lee, C. S., Field-effect flow control in a polydimethylsiloxane-based microfluidic system. *Electrophoresis* 2001, 22, (18), 3902-3907.
16. Chen, H.; Brook, M. A.; Sheardown, H. D.; Chen, Y.; Klenkler, B., Generic bioaffinity silicone surfaces. *Bioconjugate Chem.* 2006, 17, (1), 21-28.
17. Ren, T. B.; Weigel, T.; Groth, T.; Lendlein, A., Microwave plasma surface modification of silicone elastomer with Allylamine for improvement of biocompatibility. *J. Biomed. Mater. Res. A* 2008, 86A, (1), 209-219.
18. Okaniwa, M.; Ohta, Y., Novel emulsion graft copolymerization onto the silylmethyl group of poly(dimethylsiloxane). *J. Poly. Sci. A, Polym. Chem.* 1997, 35, (13), 2607-2617.
19. Owen, M. J., Siloxane Surface Activity. In *Silicon-Based Polymer Science: A Comprehensive Resource*, Zeigler, J. M.; Fearon, F. W. G., Eds. American Chemical Society: Washington, D.C., 1990; pp 705-739.
20. Owen, M. J., Surface Chemistry and Application. In *Siloxane Polymers*, S. J. Clarson, J. A. S., Ed. Prentice Hall: Englewood Cliffs, 1993; p 309.
21. Patrito, N.; McLachlan, J. M.; Faria, S, N.; Chan, J.; Norton, P. R., A novel metal-protected plasma treatment for the robust bonding of polydimethylsiloxane. *Lab on a Chip* 2007, 7, (12), 1813-1818.
22. Patrito, N.; McCague, C.; Norton, P. R.; Petersen, N. O., Spatially controlled cell adhesion via micropatterned surface modification of poly(dimethylsiloxane). *Langmuir* 2007, 23, (2), 715-719.
23. Matyjaszewski, K.; Miller, P. J.; Shukla, N.; Immaraporn, B.; Gelman, A.; Luokala, B. B.; Siclovan, T. M.; Kickelbick, G.; Valiant, T.; Hoffmann, H.; Pakula, T., Polymers at interfaces: Using atom transfer radical polymerization in the controlled growth of homopolymers and block copolymers from silicon surfaces in the absence of untethered sacrificial initiator. *Macromolecules* 1999, 32, (26), 8716-8724.
24. Houbenov, N.; Minko, S.; Stamm, M., Mixed polyelectrolyte brush from oppositely charged polymers for switching of surface charge and composition in aqueous environment. *Macromolecules* 2003, 36, 5897-5901.
25. Wagner, R.; Wu, Y.; Richter, L.; Siegel, S.; Weissmuller, J.; Reiners, J., Silicon-modified carbohydrate surfactants IX: Dynamic wetting of a perfluorinated solid surface by solutions of a siloxane surfactant above and below the critical micelle concentration. *Appl. Organomet. Chem.* 1998, 12, (12), 843-853.
26. Nikolov, A. D.; Wasan, D. T.; Chengara, A.; Koczo, K.; Policello, G. A.; Kolossvary, I., Superspreading driven by Marangoni flow. *Adv. Colloid Interface Sci.* 2002, 96, (1-3), 325-338.
27. Hill, R. M., *Silicone Surfactants*. Dekker: New York, 1999.
28. Wang, R.; Hashimoto, K.; Fujishima, A.; Chikuni, M.; Kojima, E.; Kitamura, A.; Shimohigoshi, M.; Watanabe, T., Light-induced amphiphilic surfaces. *Nature* 1997, 388, (6641), 431-432.
29. Wang, Y. X.; Deng, J. P.; Zhong, W. B.; Kong, L. B.; Yang, W. T., Facile surface superhydrophilic modification: NVP/MBA inverse microemulsion surface-grafting polymerization initiated by UV light. *Macromolecular Rapid Communications* 2005, 26, (22), 1788-1793.
30. Chang, F. M.; Sheng, Y. J.; Chen, H.; Tsao, H. K., From superhydrophobic to superhydrophilic surfaces tuned by surfactant solutions. *Applied Physics Letters* 2007, 91, (9).
31. Brook, M. A., Silicones. In *Silicon in Organic, Organometallic and Polymer Chemistry*, Wiley: New York, 2000; pp 256-308.
32. Svitova, T.; Hill, R. M.; Smirnova, Y.; Stuermer, A.; Yakubov, G., Wetting and interfacial transitions in dilute solutions of trisiloxane surfactants. *Langmuir* 1998, 14, (18), 5023-5031.
33. Mikhail, A. S.; Ranger, J. J.; Liu, L.; Longenecker, R.; Thompson, D. B.; Sheardown, H. D.; Brook, M. A., Rapid and Efficient Assembly of Functional Silicone Surfaces Protected by PEG: Cell Adhesion to Peptide-Modified PDMS. *J. Biomater. Sci. Polym. Ed.* 2009, (in press).
34. Brook, M. A.; Liu, L.; Zhao, S.; Mammo, Z. N., Etching of Silicone Elastomers: Controlled Manipulation of Surface Roughness. In *Synthesis and Properties of Silicones and Silicone-Modified Materials*, Clarson, S. J.; Fitzgerald, J. J.; Owen, M. J.; Smith, S. D.; Van Dyke, M. E., Eds. American Chemical Society Washington D.C., 2010; Vol. in press.
35. Guo, D. J.; Han, H. M.; Jing, W.; Xiao, S. J.; Dai, Z. D., Surface-hydrophilic and protein-resistant silicone elastomers prepared by hydrosilylation of vinyl poly(ethylene glycol) on hydrosilanes-poly(dimethylsiloxane) surfaces. *Colloid Surf. A-Physicochem. Eng. Asp.* 2007, 308, (1-3), 129-135.
36. Bain, A. D.; Brook, M. A.; Hazendonk, P.; Reid, D.; Stan, R. S., Analysis of the NMR spectra of some dimethylsilanes. *Magn. Reson. Chem.* 2000, 38, (10), 894-895.
37. Thompson, D. B. G., F.; Fawcett, A. S.; and Brook, M. A., Hydrolytically stable linkers for silicone carbohydrates derived from hydrodiisopropylsilanes. *Silicon Chemistry* 2008, (ASAP).
38. Chen, H.; Brook, M. A.; Chen, Y.; Sheardown, H., Surface properties of PEO-silicone composites: reducing protein adsorption. *J. Biomater. Sci.-Polym. Ed.* 2005, 16, (4), 531-548.
39. Herren, B. J.; Shafer, S. G.; Vanalstine, J.; Harris, J. M.; Snyder, R. S., CONTROL OF ELECTROOSMOSIS IN COATED QUARTZ CAPILLARIES. *J. Colloid Interface Sci.* 1987, 115, (1), 46-55.
40. Brink, C.; Osterberg, E.; Holmberg, K.; Tiberg, F., USING POLY(ETHYLENE IMINE) TO GRAFT POLY (ETHYLENE GLYCOL) OR POLYSACCHARIDE TO POLYSTYRENE. *Colloids Surf.* 1992, 66, (2), 149-156.
41. Currie, E. P. K.; Norde, W.; Stuart, M. A. C., Tethered polymer chains: surface chemistry and their impact on colloidal and surface properties. *Adv. Colloid Interface Sci.* 2003, 100, 205-265.
42. Dong, B. Y.; Jiang, H. Q.; Manolache, S.; Wong, A. C. L.; Denes, F. S., Plasma-mediated grafting of poly(ethylene glycol) on polyamide and polyester surfaces and evaluation of antifouling ability of modified substrates. *Langmuir* 2007, 23, (13), 7306-7313.
43. Zdyrko, B.; Varshney, S. K.; Luzinov, I., Effect of Molecular Weight on Synthesis and Surface Morphology of High-Density Poly(ethylene glycol) Grafted Layers. *Langmuir* 2004, 20, (16), 6727-6735.
44. Kim, K.; Shin, K.; Kim, H.; Kim, C.; Byun, Y., In situ photopolymerization of a polymerizable poly(ethylene glycol)-covered phospholipid monolayer on a methaeryloyl-terminated substrate. *Langmuir* 2004, 20, (13), 5396-5402.
45. Unsworth, L. D.; Tun, Z.; Sheardown, H.; Brash, J. L., In situ neutron reflectometry investigation of gold-chemisorbed PEO layers of varying chain density: Relationship of layer structure to protein resistance. *J. Colloid Interface Sci.* 2006, 296, (2), 520-526.

46. Zelisko, P.; Flora, K. K.; D. J, B.; Brook, M. A., Water-in-Silicone Oil Emulsion Stabilizing Surfactants Formed From Native Albumin and α,ω-Triethoxysilylpropyl-Polydimethylsiloxane. *Biomacromolecules* 2008, 9, (8), 2153-2161.
47. Jiang, R.; Jin, Q. H.; Li, B. H.; Ding, D. T.; Shi, A. C., Phase diagram of poly(ethylene oxide) and poly(propylene oxide) triblock copolymers in aqueous solutions. *Macromolecules* 2006, 39, (17), 5891-5896.
48. Yang, Z. H.; Sharma, R., Dynamics of PEO-PPO-PEO and PPO-PEO-PPO triblock copolymers at the air/water interface upon thermal stimulation. *Langmuir* 2001, 17, (20), 6254-6261.
49. Wagner, R.; Wu, Y.; Czichocki, G.; von Berlepsch, H.; Weiland, B.; Rexin, F.; Perepelittchenko, L., Silicon-modified surfactants and wetting: I. Synthesis of the single components of Silwet L77 and their spreading performance on a low-energy solid surface. *Appl. Organomet. Chem.* 1999, 13, (9), 611-620.

TABLE 1

Water wetting effects on PDMS modified with PEO[a] and with a trisiloxane surfactant[b]

|  | A250 | A350 | A550 |
|---|---|---|---|
| Grafting Percentage % | 6.89 | 3.96 | 1.91 |
| Contact Angle (°) | 83 | 87 | 90 |

|  | APS | LAPS[c] | SAPS |
|---|---|---|---|
| Grafting Percentage % | 14.1 | 18.7 | 17.1 |
| Contact Angle (°) | 0 | 69 | 73 |
| Wetting Diameter (mm)[d] | 8 | 4.5 | 4 |

[a]PEO was dissolved 50 wt % in anhydrous THF to improve the reaction; the hydrosilylation occurred over 12 hours on a silicone surface prepared with 1% DC1107.
[b]Water droplets of 0.02 ml volume were used.
[c]Although a ~2:1 mixture of the monosilyl (LAPS) and disilyl analogue was used to modify the surface, only the former compound can chemically tether to the surface.
[d]The initial radius of the wetted spot was ~1.0 mm; the final diameter was tested after 1 min.

The invention claimed is:

1. A compound of the formula (I):

$$\text{CH}_2=\text{CHCH}_2-\text{O}-\left[\text{CH}_2\text{CH}_2\text{O}\right]_n-\left[\text{CH}_2\text{CH}(\text{CH}_3)\text{O}\right]_m-R^1 \quad (I)$$

wherein
n is 6, 7, 8, 9 or 10;
m is 1, 2, 3, 4, 5 or 6; and
$R^1$ is a straight or branched chain siloxane, wherein terminal units of the siloxane have the formula $R^2R^3R^4SiO$, wherein $R^2$, $R^3$ and $R^4$ are each independently an alkyl, alkenyl or aryl group.

2. The compound of claim 1, wherein n is 7, 8 or 9.
3. The compound of claim 2, wherein n is 8.
4. The compound of claim 1, wherein m is 1, 3, 4, 5 or 6.
5. The compound of claim 4, wherein m is 1 or 3, 4 or 5.
6. The compound of claim 5, wherein m is 1 or 3.
7. The compound of claim 1, wherein $R^1$ is a siloxane comprising from 2 to 15 silicon atoms.
8. The compound of claim 7, wherein $R^1$ is a branched trisiloxane.
9. The compound of claim 1, wherein $R^1$ is a methylsiloxane.
10. The compound of claim 1, wherein $R^1$ is selected from one of the following groups:

wherein ⌇ represents the point of attachment of the group to the compound for Formula (I).

11. The compound of claim 10, wherein $R^1$ is wherein ⌇ represents the point of attachment of the group to the compound for Formula (I).

12. A method of modifying a surface of a substrate comprising grafting one or more compounds of Formula (I) as defined in claim 1 to the substrate.

13. The method of claim 12, wherein the grafting is done by reacting the substrate and the one or more compounds of Formula (I) under conditions to form a covalent attachment therebetween.

14. The method of claim 13, wherein the covalent attachment is formed by a reaction between the allyl group on the one or more compounds of Formula (I) and one or more functional groups on the substrate.

15. The method of claim 12, wherein the substrate is poly(dimethylsiloxane) (PDMS), polystyrene (PS), polypropylene (PP), polyethylene, poly(methyl methacrylate) (PMMA) or related acrylic polymers, polycarbonate (PC), polyisopropylene (PI), nylon or related polyamides, polyacylamides, fluorocarbons or mixtures thereof.

16. The method of claim 15, wherein the substrate is PDMS.

17. A substrate that has been surface modified by grafting of one or more compounds of Formula (I), as defined in claim 1, on to its surface.

18. The substrate of claim 17, wherein the substrate is PDMS.

19. The substrate of claim 17 having a water contact angle of about 10° or less.

* * * * *